(12) United States Patent
Maltz

(10) Patent No.: US 11,291,864 B2
(45) Date of Patent: Apr. 5, 2022

(54) SYSTEM AND METHOD FOR IMAGING OF MOVING SUBJECTS

(71) Applicant: SHANGHAI UNITED IMAGING HEALTHCARE CO., LTD., Shanghai (CN)

(72) Inventor: Jonathan Maltz, Concord, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 295 days.

(21) Appl. No.: 16/708,568

(22) Filed: Dec. 10, 2019

(65) Prior Publication Data

US 2021/0170198 A1    Jun. 10, 2021

(51) Int. Cl.
| G06K 9/20 | (2006.01) |
| A61N 5/10 | (2006.01) |
| G06T 7/10 | (2017.01) |
| G06T 7/70 | (2017.01) |
| G06T 7/20 | (2017.01) |

(52) U.S. Cl.
CPC ......... *A61N 5/1049* (2013.01); *A61N 5/1081* (2013.01); *G06T 7/10* (2017.01); *G06T 7/20* (2013.01); *G06T 7/70* (2017.01); *G06T 2207/10081* (2013.01); *G06T 2207/30048* (2013.01); *G06T 2207/30061* (2013.01)

(58) Field of Classification Search
CPC combination set(s) only.
See application file for complete search history.

(56) References Cited

U.S. PATENT DOCUMENTS

| 8,824,862 | B2 * | 9/2014 | Sasaki | G06F 3/04883 |
| | | | | 386/282 |
| 9,420,185 | B2 * | 8/2016 | Oh | H04N 5/2328 |
| 9,514,379 | B2 * | 12/2016 | Park | G06K 9/00342 |
| 2011/0267485 | A1 * | 11/2011 | Kane | G06T 7/529 |
| | | | | 348/222.1 |

* cited by examiner

*Primary Examiner* — Quan M Hua
(74) *Attorney, Agent, or Firm* — Metis IP LLC

(57) ABSTRACT

The present disclosure provides a method for imaging of moving subjects. The method may include determining a motion range of a region of interest (ROI) of a subject in an axial direction. The method may also include causing a radiation source to emit, at each of a plurality of axial positions relative to the subject, radiation beams to the ROI to generate an image frame of the ROI. The radiation beams corresponding to the plurality of axial positions may jointly cover the motion range of the ROI in the axial direction. The method may further include determining a position of the ROI in the axial direction based on the image frames of the ROI, and determining, based on the positions of the ROI in the axial directions, at least one time bin in which therapeutic beams are to be emitted to the ROI.

20 Claims, 11 Drawing Sheets

100

700

702 — Obtaining a time-varying motion signal representing the physiological motion via a sensor coupled to the subject 704 — Dividing the time-varying motion signal into a plurality of segments, each of the plurality of the segments corresponding to one of the plurality of time bins

902 — Causing a table to move to a table location such that the radiation source is at one of the plurality of axial positions relative to the subject 904 — Causing the radiation source to emit the radiation beams to the ROI while the table is at the table location

Causing a gantry to move to a gantry location such that the radiation source is at one of the plurality of axial positions relative to the subject — 1002

Causing the radiation source to emit the radiation beams to the ROI while the gantry is at the gantry location — 1004

FIG. 10

SYSTEM AND METHOD FOR IMAGING OF MOVING SUBJECTS

TECHNICAL FIELD

The present disclosure generally relates to systems and methods for imaging, and more particularly, to systems and methods for imaging of moving subjects.

BACKGROUND

Imaging technologies, such as the CT imaging, have been widely used in the medical field. In applications such as radiation therapy (RT) involving a moving subject, imaging may be used before treatment to determine the motion range of the treatment target and/or organs at risk (OARs) of radiation damage. Often, a treatment is planned so that therapeutic beams are applied during only a portion of a motion cycle, such as at 80% to 100% of full exhalation in a breathing cycle. It is of great importance that the portion of the motion cycle that corresponds to the motion state in which the treatment target is in the planned position are set before treatment ensues on a particular day. Therefore, it is desired to develop methods and systems for imaging of the moving subject in a better way such that the full range of motion is captured in the images.

SUMMARY

According to an aspect of the present disclosure, a method is provided. The method may be implemented on a computing device having at least one storage device storing a set of instructions, and at least one processor in communication with the at least one storage device. The method may include determining a motion range of a region of interest (ROI) of a subject in an axial direction. The ROI may move due to a physiological motion of the subject. The method may further include dividing the physiological motion into a plurality of time bins. The method may further include, in at least one of the plurality of time bins, determining a plurality of axial positions relative to the subject for a radiation source, and causing the radiation source to emit, at each of the plurality of axial positions relative to the subject, radiation beams to the ROI to generate an image frame of the ROI. The radiation beams corresponding to the plurality of axial positions may jointly cover the motion range of the ROI in the axial direction. The method may further include determining, for each of the plurality of time bins, a position of the ROI in the axial direction based on the image frames of the ROI generated in the corresponding time bin. And the method may also include determining, based on the positions of the ROI in the axial directions and among the plurality of time bins, at least one time bin in which therapeutic beams are to be emitted to the ROI.

In some embodiments, the determining a motion range of an ROI of a subject in an axial direction may include obtaining an image of the subject based on a scan of the subject, identifying the ROI in the image of the subject, and determining the motion range of the ROI based on the identified ROI.

In some embodiments, the physiological motion of the subject may include at least one of a respiration motion or a cardiac motion of the subject.

In some embodiments, the radiation source may generate X-rays with at least two different energy spectra.

In some embodiments, the dividing the physiological motion into a plurality of time bins may include obtaining a time-varying motion signal representing the physiological motion via a sensor coupled to the subject, and dividing the time-varying motion signal into a plurality of segments, each of the plurality of the segments corresponding to one of the plurality of time bins.

In some embodiments, the determining, for a radiation source, a plurality of axial positions relative to the subject may include determining an axial coverage of the radiation beams of the radiation source, and determining the plurality of axial positions for the radiation source such that the motion range of the ROI in the axial direction is within a combination of the axial coverages of the radiation source at the plurality of axial positions relative to the subject.

In some embodiments, the subject is supported by a table that may be movable in the axial direction. The causing the radiation source to emit, at each of the plurality of axial positions relative to the subject, radiation beams to the ROI to generate an image frame of the ROI may include causing the table to move to a table location such that the radiation source is at one of the plurality of axial positions relative to the subject, and causing the radiation source to emit the radiation beams to the ROI while the table is at the table location.

In some embodiments, the radiation source may be installed on a gantry that is movable in the axial direction. The causing the radiation source to emit, at each of the plurality of axial positions relative to the subject, radiation beams to the ROI to generate an image frame of the ROI may include causing the gantry to move to a gantry location such that the radiation source is at one of the plurality of axial positions relative to the subject, and causing the radiation source to emit the radiation beams to the ROI while the gantry is at the gantry location.

In some embodiments, the determining, based on the positions of the ROI in the axial directions and among the plurality of time bins, at least one time bin, in which therapeutic beams are to be emitted to the ROI may include obtaining a planned position of the ROI at which the therapeutic beams are to be emitted, determining, among positions of the ROI in the axial direction, at least one position of the ROI that matches the planned position of the ROI at which the therapeutic beams are to be emitted, and determining the at least one time bin based on the at least one matched position of the ROI.

In some embodiments, the method may further include tracking a motion of the ROI. The determining, for a radiation source, a plurality of axial positions relative to the subject may include determining the plurality of axial positions relative to the subject based on the tracked motion of the ROI.

In some embodiments, the causing the radiation source to emit, at each of the plurality of axial positions relative to the subject, radiation beams to the ROI to generate an image frame of the ROI may include causing the radiation source to emit, at each of the plurality of axial positions relative to the subject, radiation beams to the ROI from one or more angles at which the therapeutic beams are to be emitted to the ROI.

According to an aspect of the present disclosure, a system is provided. The system may include at least one storage medium including a set of instructions and at least one processor in communication with the at least one storage medium. When executing the instructions, the at least one processor may configured to direct the system to perform operations. The operations may include determining a motion range of a region of interest (ROI) of a subject in an axial direction. The ROI may move due to a physiological motion of the subject. The operations may further include dividing the physiological motion into a plurality of time bins. The operations may further include, in at least one of the plurality of time bins, determining a plurality of axial positions relative to the subject for a radiation source, and causing the radiation source to emit, at each of the plurality of axial positions relative to the subject, radiation beams to the ROI to generate an image frame of the ROI. The radiation beams corresponding to the plurality of axial positions may jointly cover the motion range of the ROI in the axial direction. The operations may further include determining, for each of the plurality of time bins, a position of the ROI in the axial direction based on the image frames of the ROI generated in the corresponding time bin. And the operations may also include determining, based on the positions of the ROI in the axial directions and among the plurality of time bins, at least one time bin in which therapeutic beams are to be emitted to the ROI.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7 is a flowchart illustrating an exemplary process for dividing a time-varying motion signal according to some embodiments of the present disclosure;

FIG. 9 is a flowchart illustrating an exemplary process for causing the radiation source to emit radiation beams according to some embodiments of the present disclosure;

FIG. 10 is a flowchart illustrating another exemplary process for causing the radiation source to emit radiation beams according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
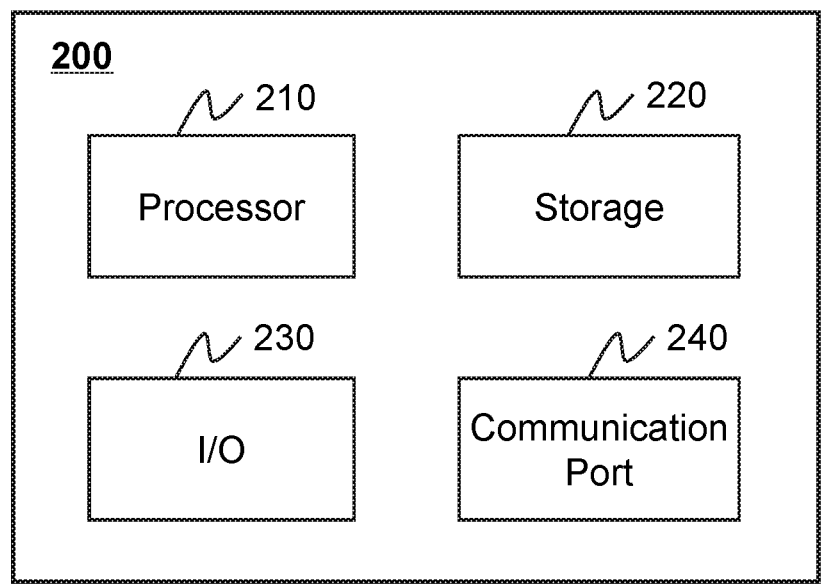
FIG. 2 is a schematic diagram illustrating an exemplary computing device on which at least a portion of the imaging system 100 can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when as used herein, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and methods for imaging, such as for disease diagnosis, physical check-up, or disease treatment. For example, the imaging systems and methods provided in the present disclosure may be used in an internal inspection (e.g., a non-invasive internal inspection) including, for the anatomical structure of one or more tissues or one or more organs, the metabolism of one or more tissues or one or more organs, the function of one or more tissues or one or more organs. The imaging system may find its applications in different fields other than the medical fields. For example, the imaging system may be used in an internal inspection (e.g., a non-invasive internal inspection) of one or more components. For example, the imaging systems and methods provided in the present disclosure may be used in flaw detection of a component of a machine, bag or luggage security scanning, failure analysis, metrology, assembly analysis, void detection, wall thickness assessment, or the like, or any combination thereof.

Some embodiments of the present disclosure provide systems and methods for imaging of a moving ROI in a subject. In some embodiments, the moving ROI may move due to a physiological motion of the subject. The methods may include determining a motion range of the moving ROI in an axial direction. The method may further include dividing the physiological motion of the subject into a plurality of time bins. In at least one of the plurality of time bins, a radiation source may emit, at a plurality of axial positions relative to the subject, radiation beams to the ROI to generate image frames of the ROI. On this occasion, the radiation beams emitted from the radiation source at the plurality of axial positions may jointly cover the axial range of the ROI wherever the ROI moves. To this end, in some embodiments, the methods may include causing the radiation source to exhaustively scan the ROI such that the motion range of the moving ROI in the axial direction are always covered by the radiation beams in each time bin. In some alternative embodiments, the methods may include causing the radiation source to actively track the axial range of the ROI in real time and cover the tracked axial range of the ROI by the radiation beams in each time bin. Then, the method may include determining, for each of the plurality of time bins, a position of the ROI in the axial direction based on the image frames of the ROI generated in the corresponding time bin. The method may further include determining, based on the positions of the ROI in the axial direction and among the plurality of time bins, at least one time bin in which therapeutic beams are to be emitted to the ROI.

The following description is provided to facilitate better understanding of methods and/or systems for imaging of moving ROIs. The term "image" used in this disclosure may refer to a 2D image, a 3D image, a 4D image, and/or any related image data (e.g., projection data and/or corresponding image data). The image data may correspond to a distribution of the degree of absorption of radiation beams by different anatomical structures of the subject (e.g., a patient). The projection data corresponding to the image data may refer to a sum or line integral of linear attenuation coefficient(s) along a plurality of radiation beam directions.

The following descriptions in connection with a CT imaging system are provided for illustration purposes. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
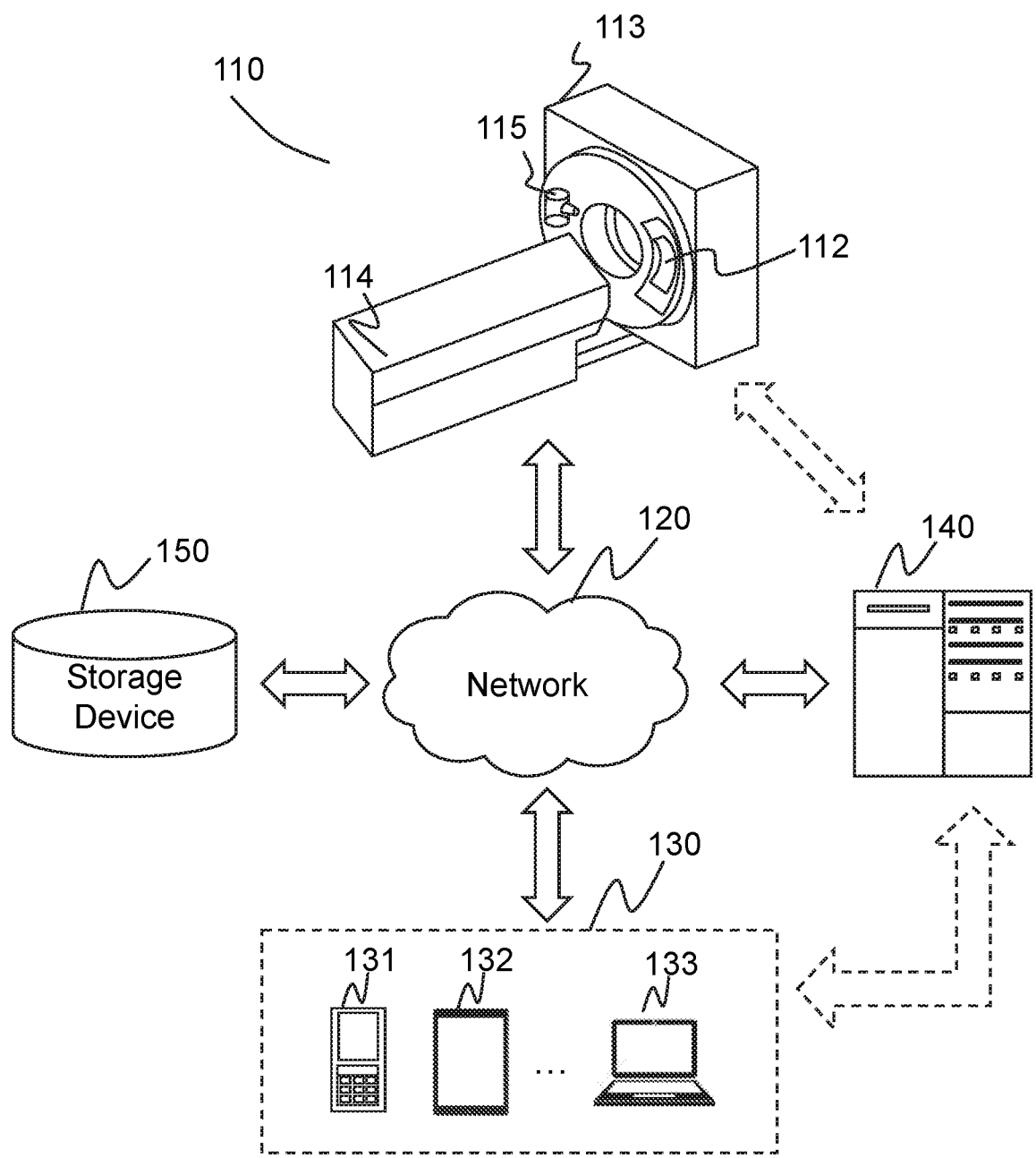
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. The imaging system 100 may include an imaging device 110, a network 120, one or more terminals 130, a processing device 140, and a storage device 150.

The imaging device 110 may be a computed tomography (CT) imaging device. The imaging device 110 may include a gantry 113, a detector 112, a table 114, and a scanning source 115. The gantry 113 may support the detector 112 and the scanning source 115. A subject may be placed on the table 114 for scanning. The scanning source 115 may emit X-rays to the subject. The detector 112 may detect attenuated X-rays. The attenuated X-rays may further be processed and converted to image data for image reconstruction. Merely by way of example with reference to the imaging system 100, the X-rays may be generated by the scanning source 115 according to the bremsstrahlung principle. The detector 112 may include a semiconductor detector, a gas detector, or a scintillation detector, etc. In some embodiments, the detector 112 may include a plurality of detector units, and the plurality of detector units may be arranged in any suitable manner. For example, the plurality of detector units may be arranged on a plane, and the detector 112 may be a flat panel detector. As another example, the plurality of detector units may be arranged on an arc surface, and the detector 112 may be an arc-shaped detector.

In some embodiments, a treatment device (not shown in the figure) may be added to the imaging system 100. The treatment device may include a treatment radiation source, a gantry, a collimator, or the like, or a combination thereof. The treatment radiation source may be a linear accelerator (LINAC). The collimator may control the shape of the radioactive rays generated by the treatment radiation source. In some embodiments, the imaging device 110 and the treatment device may share a same gantry. For example, the treatment radiation source may be mounted on the gantry 113. A subject may be placed on the table 114 for treatment and/or scan. Merely by way of example, the imaging system 100 may be an RT-CT system. The imaging device 110 described herein may be applied in subject positioning and/or verification in image-guided radiation therapy (IGRT). The image for guiding therapeutic beams may be generated based on the image data processed/converted from the attenuated X-rays detected by the detector 112 of the imaging device 110.

The network 120 may include any suitable network that can facilitate the exchange of information and/or data for the imaging system 100. In some embodiments, one or more components of the imaging system 100 (e.g., the imaging device 110, the terminal(s) 130, the processing device 140, the storage device 150, etc.) may exchange information and/or data with one or more other components of the imaging system 100, or an external device (e.g., an external storage device) via the network 120. For example, the processing device 140 may obtain projection data from the imaging device 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 702.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

Figure 3:
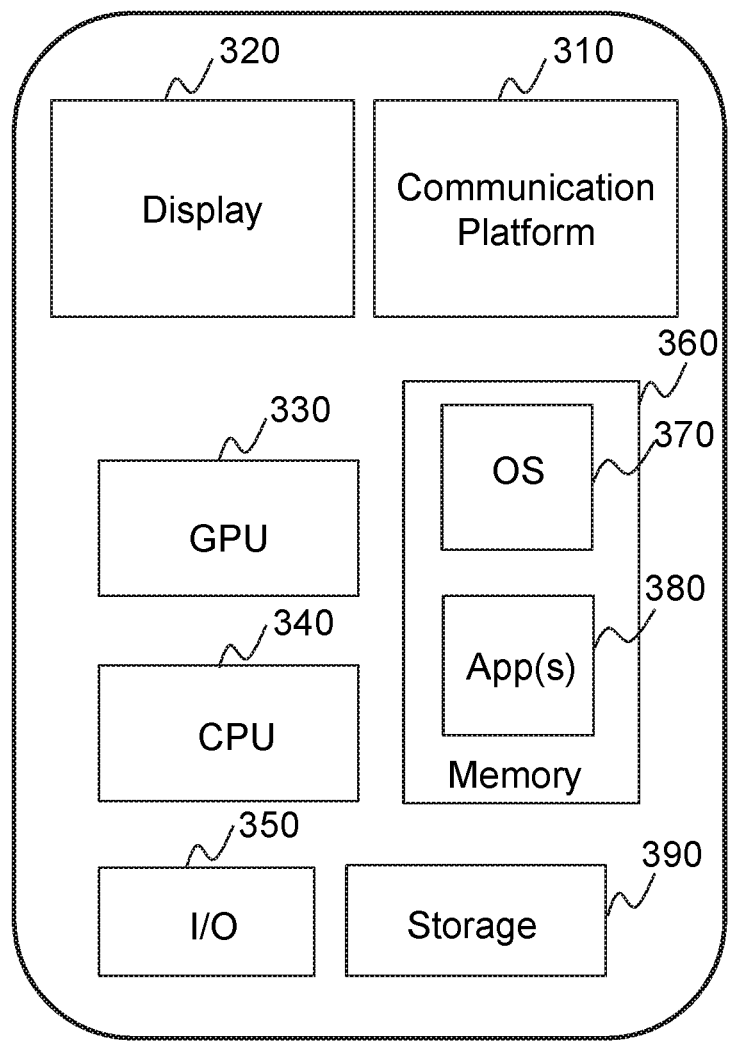
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data, images, and/or information obtained from the imaging device 110, the terminal(s) 130, the storage device 150, an external device, etc. In some embodiments, the processing device 140 may be a single server or a server group. The server group may be centralized or distributed. In some embodiments, the processing device 140 may be local to or remote from other components of the imaging system 100 (e.g., the imaging device 110). For example, the processing device 140 may access, via the network 120, data, images, and/or information stored in the imaging device 110, the terminal(s) 130, the storage device 150, an external device, etc. As another example, the processing device 140 may be directly connected to the imaging device 110, the terminal(s) 130, and/or the storage device 150 to access stored data, images, and/or information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal(s) 130). In some embodiments, the storage device 150 may be part of the processing device 140.

FIG. 2 is a schematic diagram illustrating an exemplary computing device 200 on which at least a portion of the imaging system 100 can be implemented, according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process motion data obtained from the imaging device 110, the terminal(s) 130, the storage device 150, and/or any other component of the imaging system 100. As another example, the processor 210 may process image(s) obtained from the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus, operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the imaging system 100, an external device, etc. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for imaging and/or determining at least one time bin in which therapeutic beams are to be emitted to the ROI.

The I/O 230 may input and/or output signals, data, information, etc. In some embodiments, the I/O 230 may enable user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
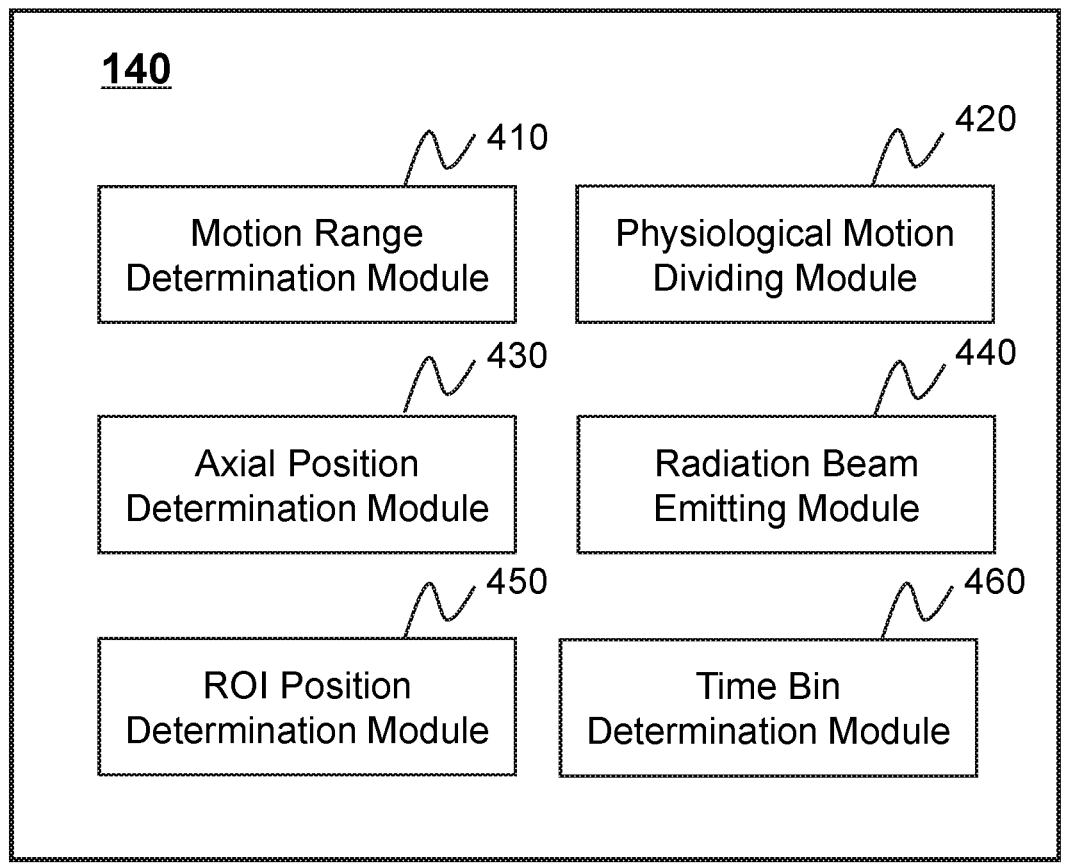
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include a motion range determination module 410, a physiological motion dividing module 420, an axial position determination module 430, a radiation beam emitting module 440, a ROI position determination module 450, and a time bin determination module 460.

The processing device 140 may be implemented on various components (e.g., the computing device 200 as illustrated in FIG. 2, the mobile device 300 as illustrated in FIG. 3).

The motion range determination module 410 may be configured to determine a motion range of a region of interest (ROI) of a subject in an axial direction. In some embodiments, the ROI may refer to a physical portion of the subject that is supposed to be illuminated and/or treated by therapeutic beams in a therapeutic process. In some embodiments, the ROI may move due to a physiological motion of the subject. The motion range of the ROI in the axial direction may refer to the entire range of motion of the ROI in the axial direction during a full cycle of the physiological motion. In some embodiments, the motion range of the ROI in the axial direction may be represented in a coordinate system. In some embodiments, to determine the motion range of the ROI of the subject in the axial direction, the motion range determination module 410 may be configured to obtain an image of the subject based on a scan of the subject, identify the ROI in the image of the subject, and determine the motion range of the ROI based on the identified ROI.

The physiological motion dividing module 420 may be configured to divide the physiological motion into a plurality of time bins. In some embodiments, each of the plurality of time bins may be short enough such that in the each of the plurality of time bins, the ROI of the subject may be considered to be static or approximately static. For each of the plurality of time bins, data obtained therein may be used to reconstruct an image, which may be used to provide information of the ROI in the corresponding time bin. In some embodiments, to divide the physiological motion into a plurality of time bins, the physiological motion dividing module 420 may be configured to obtain a time-varying motion signal representing the physiological motion via a sensor coupled to the subject, and divide the time-varying motion signal into a plurality of segments.

The axial position determination module 430 may be configured to determine a plurality of axial positions relative to the subject for a radiation source. In some embodiments, the radiation source may generate X-rays with at least two different energy spectra. In some embodiments, to determine the plurality of axial positions relative to the subject, the axial position determination module 430 may be configured to determine an axial coverage of the radiation beams of the radiation source, and determine the plurality of axial positions for the radiation source such that the motion range of the ROI in the axial direction is within a combination of the axial coverages of the radiation source at the plurality of axial positions relative to the subject. In some embodiments, to determine the plurality of axial positions relative to the subject, the axial position determination module 430 may also be configured to track the motion of the ROI in real time, and determine the plurality of axial positions relative to the subject based on the real-time axial range of the ROI.

The radiation beam emitting module 440 may be configured to cause the radiation source to emit, at each of the plurality of axial positions relative to the subject, radiation beams to the ROI to generate an image frame of the ROI. In some embodiments, the subject may be supported by a table that is movable in the axial direction. The radiation beam emitting module 440 may be configured to cause the table to move to a table location such that the radiation source is at one of the plurality of axial positions relative to the subject, and cause the radiation source to emit the radiation beams to the ROI while the table is at the table location. In some embodiments, the radiation source may be installed on a gantry that is movable in the axial direction. The radiation beam emitting module 440 may be configured to cause the gantry to move to a gantry location such that the radiation source is at one of the plurality of axial positions relative to the subject, and cause the radiation source to emit the radiation beams to the ROI while the gantry is at the gantry location. In some embodiments, the radiation beam emitting module 440 may be configured to cause the radiation source to emit, at each of the plurality of axial positions relative to the subject, the radiation beams to the ROI from one or more angles at which the therapeutic beams are to be emitted to the ROI. In this way, a motion trajectory of the ROI may be most relevantly determined from a point-of-view corresponding to the one or more angles of a planned therapeutic beam entry.

The ROI position determination module 450 may be configured to determine, for each of the plurality of time bins, a position of the ROI based on the image frames of the ROI generated in the corresponding time bin. In some embodiments, for each of the plurality of time bins, the ROI position determination module 450 may be configured to identify the ROI in each of the image frames of the ROI generated in the corresponding time bin. Alternatively, the ROI position determination module 450 may be configured to synthesize the plurality of image frames generated in a same time bin to obtain a synthesized image that represents the whole ROI, and then identify the whole ROI in the synthesized image. In some embodiments, the ROI position determination module 450 may be further configured to determine a position of the ROI based on the identified ROI in each of the image frames.

The time bin determination module 460 may be configured to determine, based on the positions of the ROI and among the plurality of time bins, at least one time bin in which therapeutic beams are to be emitted to the ROI. In some embodiments, to determine the at least one time bin, the time bin determination module 460 may be configured to obtain a planned position of the ROI at which the therapeutic beams are to be emitted, determine, among the positions of the ROI, at least one position of the ROI that matches the planned position of the ROI at which the therapeutic beams are to be emitted, and determine the at least one time bin based on the at least one matched position of the ROI.

Figure 5:
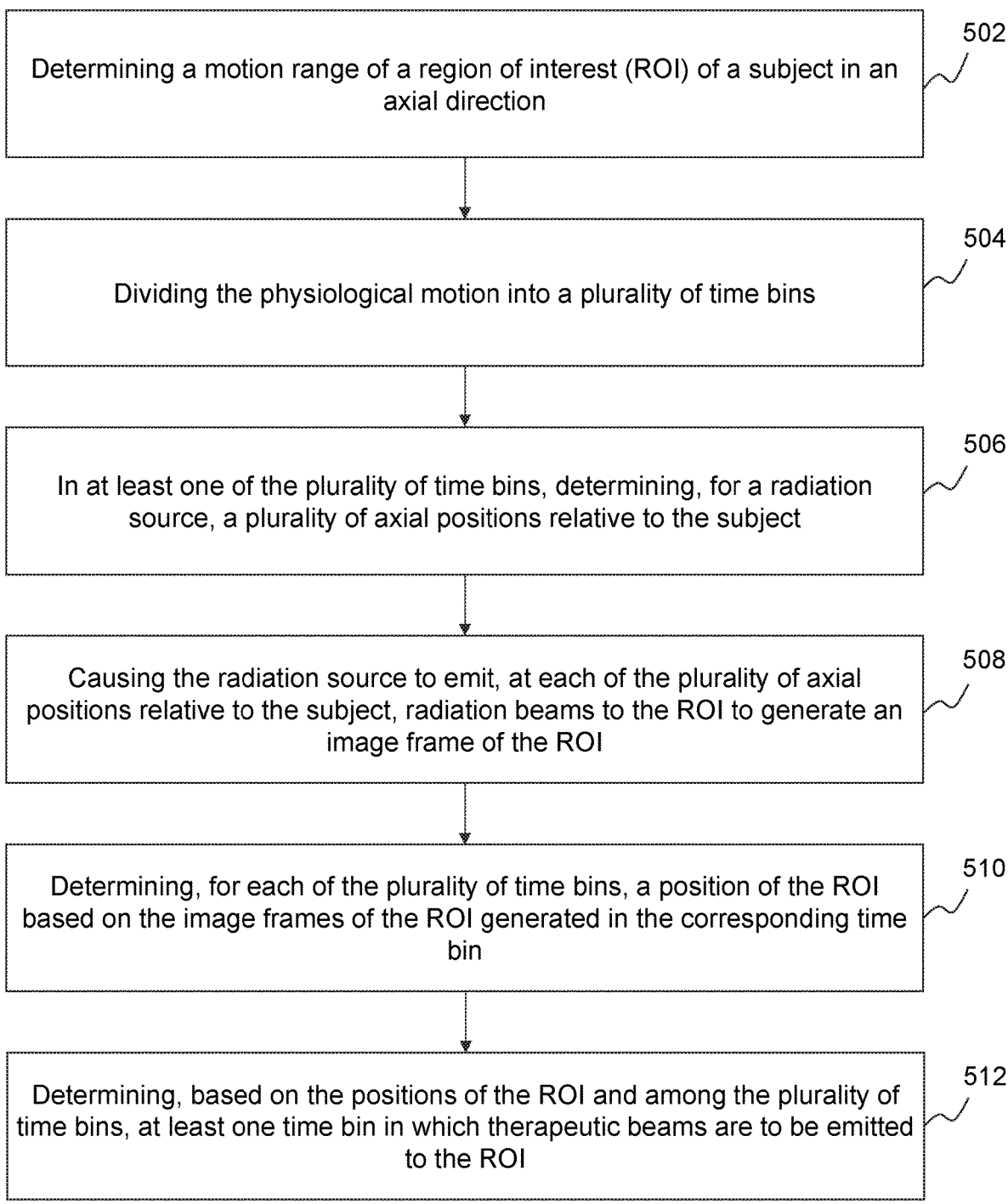
FIG. 5 is a flowchart illustrating an exemplary process for determining at least one time bin in which therapeutic beams are to be emitted to a region of interest (ROI) according to some embodiments of the present disclosure.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. Merely by way of example, the processing device 140 may include one or more other modules. How- FIG. 5 is a flowchart illustrating an exemplary process 500 for determining at least one time bin in which therapeutic beams are to be emitted to the ROI according to some embodiments of the present disclosure. In some embodiments, at least part of the process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order of the operations of the process 500 as illustrated in FIG. 5 and described below is not intended to be limiting.

In 502, the processing device 140 (e.g., the motion range determination module 410) may determine a motion range of a region of interest (ROI) of a subject in an axial direction.

In some embodiments, the subject may be biological or non-biological. Merely by way of example, the subject may include a patient, a man-made subject, etc. As another example, the subject may include a specific portion, organ, and/or tissue of a patient. Specifically, the subject may include a head, a brain, a neck, a body, a shoulder, an arm, a thorax, a heart, a stomach, a blood vessel, a soft tissue, a knee, a foot of a patient, or the like, or any combination thereof. In some embodiments, the region of interest (ROI) may refer to a physical portion (e.g., a tissue, an organ, a portion of a tissue, a portion of an organ, etc.) of the subject that is supposed to be illuminated and/or treated by therapeutic beams in a therapeutic process. For illustration purpose, assuming that the subject is a patient, the ROI may be a tumor that is on a specific organ of the patient and is to be illuminated and/or treated by therapeutic beams.

In some embodiments, the ROI may move due to a physiological motion of the subject. Exemplary physiological motion of the subject may include a respiration motion or a cardiac motion of the subject. Merely by way of example, due to a cardiac motion, an ROI on the heart or an organ (e.g., the left lung) near the heart may move with the beat of the heart. As another example, due to the respiration motion, an ROI on the lung may be located in different positions at different phases of the respiratory state (e.g., an exhalation state, an inhalation state).

The motion range of the ROI in the axial direction may refer to the entire range of motion of the ROI in the axial direction during a full cycle of the physiological motion. The axial direction may refer to the direction of the relative movement between the table 114 and the scanning source 115 during the scanning, which is identical to the direction pointing from the head to the feet when a patient lies on the table 114 for scanning. The motion range of the ROI may be determined such that, at any time point in the full cycle of the physiological motion, any part of the ROI is within the motion range of the ROI. In some embodiments, the processing device 140 (e.g., the motion range determination module 410) may determine a coordinate system for representing the motion range of the ROI in the axial direction. The coordinate system may have any number of dimensions and the dimensions may be in any direction. Exemplary coordinate system may include a world coordinate system including three dimensions, an image coordinate system, or the like, or any combination thereof. The coordinate origin of the coordinate system may be located at any suitable position. For example, the coordinate origin of the world coordinate system may be located at the isocenter of the imaging device 110.

In some embodiments, the processing device 140 may determine the motion range of the ROI in the axial direction via one or more images representing the ROI. The one or more images representing the ROI may be obtained by performing a scan on the subject using the imaging device 110 in at least one full cycle of the physiological motion. For example, the scanning source 115 may emit X-rays to scan the subject (e.g., the head, a breast, etc., of a patient) located on the table 114. The detector 112 may detect one or more X-rays emitted from the scanning source 115 or scattered by the subject to obtain projection values. Further, the processing device 140 may reconstruct the one or more images representing the ROI based on the projection values using a reconstruction algorithm. Exemplary reconstruction algorithms may include an iterative reconstruction algorithm (e.g., a statistical reconstruction algorithm), a Fourier slice theorem algorithm, a fan-beam reconstruction algorithm, an analytic reconstruction algorithm, an algebraic reconstruction technique (ART), a simultaneous algebraic reconstruction technique (SART), a filtered back projection (FBP) technique, a Feldkamp-Davis-Kress (FDK) reconstruction technique, or the like, or any combination thereof.

In some embodiments, the one or more images may include a 3D CT image, a 4D CT image, cine images, or the like, or any combination thereof. The processing device 140 (e.g., the motion range determination module 410) may identify the ROI in the one or more images and further determine the motion range of the ROI based on the identified ROI. For example, cine imaging (or 4D CT scanning) may be performed by the radiation source over at least one full cycle of the physiological motion, and the motion range of the ROI can be identified from the cine images (or the 4D CT image) accordingly. More descriptions regarding the determination of the motion range of the ROI may be found elsewhere in the present disclosure. See, e.g., FIG. 6 and the descriptions thereof.

In 504, the processing device 140 (e.g., the physiological motion dividing module 420) may divide the physiological motion into a plurality of time bins.

In some embodiments, each of the plurality of time bins may be short enough such that in the each of the plurality of time bins, the ROI of the subject may be considered to be static or approximately static. For each of the plurality of time bins, data (e.g., projection values) obtained therein may be used to reconstruct an image, which may be used to provide information of the ROI in the corresponding time bin. Exemplary information of the ROI may include a position of the ROI, a profile of the ROI, a size of the ROI, or the like, or any combination thereof. In a specific embodiment, a full cycle of a respiration motion may typically last 2-6 seconds. The full cycle of the respiration motion may be divided into, for example, 10 time bins, and thus each time bin may span 200-600 ms. In each time bin, the ROI of the subject may be considered to be static or approximately static, and therefore artifacts or blurs in the image reconstructed from data generated in that time bin may be eliminated.

In some embodiments, to divide the physiological motion into a plurality of time bins, the processing device 140 (e.g., the physiological motion dividing module 420) may obtain a time-varying motion signal representing the physiological motion via a sensor coupled to the subject, and divide the time-varying motion signal into a plurality of segments. In some alternative embodiments, the processing device 140 (e.g., the physiological motion dividing module 420) may extract a motion signal from cine images or a 4D CT image of the subject to represent the physiological motion of the subject, and divide the extracted motion signal into a plurality of segments. Each of the plurality of the segments may correspond to one of the plurality of time bins. More descriptions regarding the dividing the physiological motion may be found elsewhere in the present disclosure. See, e.g., FIG. 7 and the descriptions thereof.

In some embodiments, the physiological motion may be divided into the plurality of time bins evenly or unevenly. For example, in one cycle of the respiration motion, the respiration motion may be divided evenly such that all time bins have an identical time span (e.g., 300 ms). As another example, in one cycle of the respiration motion, the respiration motion may be divided unevenly such that a time bin corresponding to the exhalation state (e.g., at 80% to 100% of full exhalation) has a larger time span than a time bin corresponding to another breathing state (e.g., the inhalation state).

In 506, in at least one of the plurality of time bins, the processing device 140 (e.g., the axial position determination module 430) may determine, for a radiation source, a plurality of axial positions relative to the subject.

In some embodiments, the radiation source (e.g., the scanning source 115 of the imaging device 110) may generate X-rays with at least two different energy spectra. Specifically, the imaging device 110 may include a multiple energy CT, a multiple spectral CT, or the like. Multiple energy imaging may be achieved using a multilayer detector. The multiple energy CT may include a dual energy CT which uses fast switching of two energy spectra. The multiple spectral CT may include a spectrally-sensitive CT. In some embodiments, the contrast in images obtained by performing a scan using the radiation source generating X-rays with at least two different energy spectra may be improved. For example, overlying ribs in lung images obtained in the dual energy CT may be removed (or distinguishable) from the lung images, which may better reveal an ROI (e.g., a tumor) in the lung region.

In some embodiments, an axial coverage of the radiation beams (also referred to as the axial field of view (FOV)) emitted by the radiation source is not wide enough to cover the axial range of the ROI. In such case, the processing device 140 may cause the radiation source to perform multiple scans at different axial positions relative to the subject such that the axial range of the ROI may be completely included in the joint axial coverage of the radiation beams. To this end, in some embodiments, the processing device 140 (e.g., the axial position determination module 430) may determine the plurality of axial positions for the radiation source such that the entire motion range of the ROI in the axial direction is within a combination of the axial coverages of the radiation source at the plurality of axial positions relative to the subject. For brevity, the scanning of the radiation source in one time bin to completely cover the entire motion range of the ROI in the axial direction may be referred to as "exhaustive scan". In some alternative embodiments, the processing device 140 (e.g., the axial position determination module 430) may actively track the ROI and determine the plurality of axial positions for the radiation source such that the real-time axial range of the ROI, which may be a portion of the entire motion range, is within a combination of the axial coverages of the radiation source at the plurality of axial positions relative to the subject. For brevity, the scanning of the radiation source in one time bin to actively track and cover the real-time axial range of the ROI may be referred to as "predictive scan".

In some embodiments, the plurality of axial positions of the radiation source relative to the subject may vary in steps or continuously. For example, the plurality of axial positions relative to the subject may continuously change while the radiation source is emitting the radiation beams during each time bin. As another example, the plurality of axial positions relative to the subject may be discrete positions and the radiation source may emit the radiation beams only when it reaches the designated positions. More descriptions regarding the determination of the axial positions for the radiation source may be found elsewhere in the present disclosure. See, e.g., FIG. 8 and the descriptions thereof.

In 508, the processing device 140 (e.g., the radiation beam emitting module 440) may cause the radiation source to emit, at each of the plurality of axial positions relative to the subject, radiation beams to the ROI to generate an image frame of the ROI.

The radiation source (e.g., the scanning source 115) may include an X-ray tube which may generate X-rays with a power supply provided by a voltage generator. Specifically, the X-ray tube may at least include an anode and a cathode. The cathode may include one or more filaments (e.g., a tungsten wire, an iridium wire, a nickel wire, a molybdenum wire) configured to emit free electrons. The free electrons may be accelerated in an electric field between the cathode and the anode to form an electron beam striking the anode to further generate radioactive rays such as X-rays. The anode may be made of an electrically conductive material, and may have a high mechanical strength under a high temperature and have a high melting point. Exemplary materials may include titanium zirconium molybdenum (TZM), ferrum, cuprum, tungsten, graphite, or the like, or an alloy thereof, or any combination thereof. In a dual energy CT system with a single radiation source (e.g., the scanning source 115), an X-ray tube included in the single radiation source may generate X-rays with a power supply provided by a voltage generator. The power supply provided by the voltage generator may rapidly switch between a low X-ray tube voltage and a high X-ray tube voltage, and then X-rays with two different energy spectra may be generated to perform a scan on the ROI.

In some embodiments, when the radiation source emits radiation beams to the ROI at each of the plurality of axial positions relative to the subject, the detector may detect one or more X-rays emitted from the scanning source or scattered by the ROI to obtain projection values. The projection values may be transmitted to the processing device 140 for generating an image frame. In some embodiments, the processing device 140 may reconstruct an image frame based on the projection values using a reconstruction algorithm. Exemplary reconstruction algorithms may include an iterative reconstruction algorithm (e.g., a statistical reconstruction algorithm), a Fourier slice theorem algorithm, a fan-beam reconstruction algorithm, an analytic reconstruction algorithm, an algebraic reconstruction technique (ART), a simultaneous algebraic reconstruction technique (SART), a filtered back projection (FBP) technique, a Feldkamp-Davis-Kress (FDK) reconstruction technique, or the like, or any combination thereof.

In some embodiments, the radiation beams emitted by the radiation source at a specific axial position relative to the subject may cover a portion of the ROI in the axial direction. Correspondingly, an image frame corresponding to the radiation source at the specific axial position may include the information of the portion of the ROI. The radiation beams emitted by the radiation source at the plurality of axial positions may jointly cover the motion range or the real-time axial range of the ROI in the axial direction. Correspondingly, the image frames corresponding to the radiation source at the plurality of axial positions relative to the subject may jointly include the whole information of the ROI in the axial direction.

In some embodiments, the subject may be supported by a table (e.g., the table 114 of the imaging device 110) that is movable in the axial direction. The processing device 140 (e.g., the radiation beam emitting module 440) may cause the table to move to a table location such that the radiation source is at one of the plurality of axial positions relative to the subject. And the processing device 140 (e.g., the radiation beam emitting module 440) may further cause the radiation source to emit the radiation beams to the ROI while the table is at the table location. In some alternative embodiments, the radiation source may be installed on a gantry (e.g., the gantry 113 of the imaging device 110) that is movable in the axial direction. The processing device 140 (e.g., the radiation beam emitting module 440) may cause the gantry to move to a gantry location such that the radiation source is at one of the plurality of axial positions relative to the subject. And the processing device 140 (e.g., the radiation beam emitting module 440) may further cause the radiation source to emit the radiation beams to the ROI while the gantry is at the gantry location.

In some embodiments, the processing device 140 may cause the radiation source to emit, at each of the plurality of axial positions relative to the subject, the radiation beams to the ROI from one or more angles at which the therapeutic beams are to be emitted to the ROI. The therapeutic beams may include X-ray beams, charged particle beams, neutron beams, ultrasound beams, or the like, or any combination thereof, which may be used to deliver a treatment on the ROI. In some embodiments, the one or more angles may be obtained from a treatment plan in which a planned therapeutic beam entry may be pre-determined. As used herein, each of the one or more angles may correspond to a discrete angle value or an angular range. In this way, a motion trajectory of the ROI may be most relevantly determined from a point-of-view corresponding to the one or more angles of the planned therapeutic beam entry (beam's-eye-view imaging).

In 510, the processing device 140 (e.g., the ROI position determination module 450) may determine, for each of the plurality of time bins, a position of the ROI based on the image frames of the ROI generated in the corresponding time bin.

In some embodiments, as illustrated in operation 504, each of the plurality of time bins may be short enough such that in each time bin, the ROI of the subject may be considered to be static or approximately static. For each of the plurality of time bins, the processing device 140 (e.g., the ROI position determination module 450) may identify the ROI in each of the image frames of the ROI generated in the corresponding time bin. Alternatively, the processing device 140 (e.g., the ROI position determination module 450) may synthesize the plurality of image frames generated in a same time bin to obtain a synthesized image that represents the whole ROI, and then identify the whole ROI in the synthesized image. Exemplary techniques for identifying the ROI in each of the image frames or in the synthesized image may include an image segmentation technique, a manual annotation technique, a machine learning technique, or the like, or any combination thereof. Furthermore, the processing device 140 (e.g., the ROI position determination module 450) may determine a position of the ROI based on the identified ROI in each of the image frames. In some embodiments, the position of the ROI in the axial direction may include a position of the ROI relative to other organs/tissues in the subject, a position of the ROI relative to the radiation source that emits the therapeutic beams, a position of the ROI relative to other components of the imaging device 110 (e.g., the gantry 113), or the like, or a combination thereof. The position of the ROI may be represented using at least one set of coordinates. For example, the position of the ROI may be represented using a world coordinate system or an image coordinate system.

In 512, the processing device 140 (e.g., the time bin determination module 460) may determine, based on the positions of the ROI and among the plurality of time bins, at least one time bin in which therapeutic beams are to be emitted to the ROI.

In some embodiments, the processing device 140 (e.g., the time bin determination module 460) may determine the at least one time bin that corresponds to the ROI being in a planned position at which the therapeutic beams are to be emitted. As such, the therapeutic beams may be emitted to the ROI when the ROI moves to the planned position (e.g., the position designated in a treatment plan) such that therapeutic beams may be accurately emitted to the ROI and the treatment may be accurately delivered to the ROI, which may reduce the dose of X-rays exposed to other parts of the subject (e.g., an organ at risk).

Specifically, the processing device 140 (e.g., the time bin determination module 460) may obtain a planned position of the ROI at which the therapeutic beams are to be emitted. Then the processing device 140 (e.g., the time bin determination module 460) may determine, among the positions of the ROI, at least one position of the ROI that matches the planned position of the ROI at which the therapeutic beams are to be emitted. Furthermore, the processing device 140 (e.g., the time bin determination module 460) may determine the at least one time bin based on the at least one matched position of the ROI. More descriptions regarding the determination of the at least one time bin may be found elsewhere in the present disclosure. See, e.g., FIG. 11 and the descriptions thereof.

It should be noted that the above descriptions of the process 500 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 500 may include one or more other operations. However, those variations and modifications also fall within the scope of the present disclosure. For example, as illustrated in the operation 502, the motion range of the ROI of the subject in the axial direction may be determined. Persons having ordinary skills in the art may understand that, the motion range of the ROI may also be represented in 2D (e.g., in the axial direction and a lateral direction) and/or 3D (in the axial direction, a lateral direction and a vertical direction). For example, the processing device 140 may determine the motion range of the ROI in the lateral direction and/or the vertical direction. Then, the processing device 140 may further determine a plurality of positions of the radiation source relative to the subject in the lateral direction, and/or in the vertical direction, such that the motion range of the ROI in the lateral direction, and/or the vertical direction may also be completely covered by the radiation beams in each time bin. In some embodiments, by adjusting the position of the radiation source in the lateral direction and/or the vertical direction when the radiation source emits the radiation beams, it may have the advantage of allowing imaging of the ROIs close to the edge of the transaxial FOV of the radiation beams.

In some embodiments, to perform the predictive scan, the processing device 140 may actively track the ROI and determine the plurality of axial positions for the radiation source according to various techniques. For example, the processing device 140 may detect motion vectors between cine images of the ROI. The processing device 140 may further input the detected motion vectors to a predictor to predict the motion of the ROI. The predicted motion may include, for example, the predicted axial positions of the ROI during a cycle of the physiological motion. Then, in each time bin, the processing device 140 (e.g., the radiation beam emitting module 440) may cause the radiation source to emit, at multiple axial positions relative to the subject, radiation beams to completely cover the ROI at the corresponding predicted axial position to generate image frames of the ROI. In some embodiments, if a subject is instructed to hold his/her breath at a certain level of inhalation or exhalation during the imaging of the ROI, the operation of actively tracking the ROI may be omitted since the motion of the ROI associated with the held breath of the subject may be ignored.

As another example, an implanted radio frequency (RF) beacon (e.g., used in a Calypso system) may be used by way of surgical procedures to track the ROI. As still another example, an integrated magnetic resonance (MR) system may be used to present the real-time visualization of the ROI. As still another example, a radiation therapy system that has an attached kilovoltage (kV) imaging system and/or a megavoltage (MV) imaging system may be used to perform pretreatment cine imaging of the ROI to provide position information of the ROI.

Figure 6:
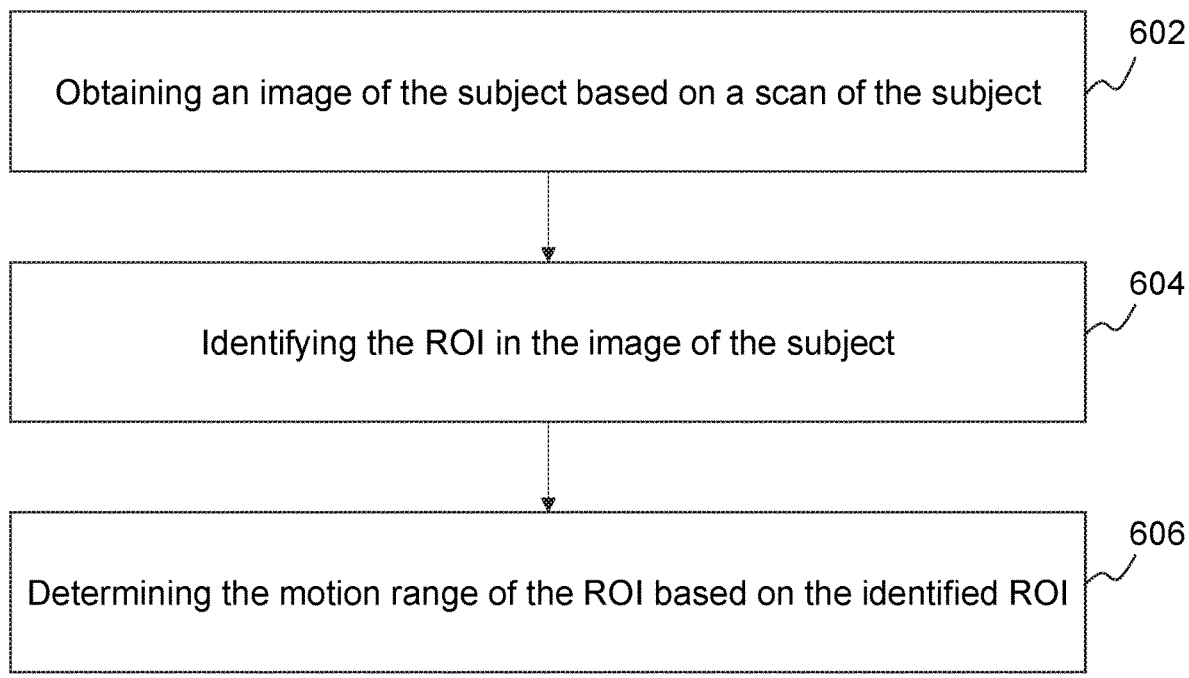
FIG. 6 is a flowchart illustrating an exemplary process for determining a motion range of the ROI according to some embodiments of the present disclosure.

FIG. 6 is a flowchart illustrating an exemplary process 600 for determining a motion range of the ROI according to some embodiments of the present disclosure. In some embodiments, at least part of the process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order of the operations of the process 600 as illustrated in FIG. 6 and described below is not intended to be limiting. In some embodiments, the operation 502 may be achieved according to the process 600.

In 602, the processing device 140 (e.g., the motion range determination module 410) may obtain an image of the subject based on a scan of the subject.

In some embodiments, processing device 140 (e.g., the motion range determination module 410) may obtain the image of the subject by performing a scout scan of the subject using the imaging device 110. For example, in any one of a CT imaging system, a PET-CT imaging system, and a CT-linac system, the processing device 140 may move the subject to a CT imaging position to perform the scout scan.

In some embodiments, the obtained image may be a single image frame. For example, the obtained image may include a 3D CT image. The single image frame may indicate the motion state of the subject (e.g., the position of an ROI in the subject, the size of the ROI in the subject, the shape of the ROI in the subject) at a specific time point.

In some embodiments, the obtained image may include multiple image frames. For example, the obtained image may include cine images, a 4D CT image, or the like, or any combination thereof. Specifically, the multiple image frames may indicate the varying motion state of the subject (e.g., the position of an ROI in the subject, the size of the ROI in the subject, the shape of the ROI in the subject) during at least one full cycle of the physiological motion of the subject. In some embodiments, the multiple image frames may be correlated with the physiological motion of the subject. For example, the multiple image frames and a respiration motion signal representing the physiological motion of the subject may be referenced to a common timebase for further processing. More descriptions regarding the respiration motion signal may be found elsewhere in the present disclosure. See, e.g., FIG. 7 and relevant descriptions thereof.

In 604, the processing device 140 (e.g., the motion range determination module 410) may identify the ROI in the image of the subject.

In some embodiments, exemplary techniques for identifying the ROI in each image frame may include an image segmentation technique, a manual annotation technique, a machine learning technique, or the like, or any combination thereof. In some embodiments, the image segmentation technique may include a threshold-based segmentation technique, a region-based segmentation technique, an edge-based segmentation technique, a segmentation technique based on specific theories, a segmentation technique based on genetic algorithms, a segmentation technique based on wavelet transforms, a segmentation technique based on clustering analysis, a segmentation technique based on mathematical morphology, a segmentation technique based on artificial neural networks, or the like, or any combination thereof. In some embodiments, the manual annotation technique may include a manual annotation technique and a semi-manual annotation technique. For example, in a manual annotation technique, an operator may annotate an image based on the digital imaging and communications in medicine (DICOM). In some embodiments, in a machine learning technique, a trained machine learning model may be used to identify the ROI in the image of the subject. For example, images with labeled ROIs may be used as training samples for training the machine learning model. Then the trained machine learning model may be used to identify one or more ROIs in an input image of the subject.

In some embodiments, in the case that the obtained image includes multiple image frames, the processing device 140 may identify the ROI in different image frames such that the motion states of the ROI at different time points may be acquired.

In 606, the processing device 140 (e.g., the motion range determination module 410) may determine the motion range of the ROI based on the identified ROI.

In some embodiments, the processing device 140 (e.g., the motion range determination module 410) may determine the motion range of the ROI in a coordinate system. The motion range of the ROI may be represented using one or more set of coordinates in the coordinate system. For example, the motion range of the ROI in the axial direction may be delimited by two axial coordinates. For brevity, the two axial coordinates may be described as a superior axial coordinate and an inferior axial coordinate.

In the case that the obtained image includes multiple image frames, the processing device 140 (e.g., the motion range determination module 410) may determine the axial position of the ROI in each of the multiple image frames. Then, the processing device 140 (e.g., the motion range determination module 410) may determine the superior axial coordinate and the inferior axial coordinate of the motion range of the ROI on the basis that all the axial positions of the ROI are always within the range delimited by the superior axial coordinate and the inferior axial coordinate.

In the case that the obtained image is a single image frame, the processing device 140 (e.g., the motion range determination module 410) may determine the axial position of the ROI in the single image frame, and estimate the motion range of the ROI by, for example, extending the range of the axial position of the ROI in the single image frame.

It should be noted that the above descriptions of the process 600 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 600 may include one or more other operations. However, those variations and modifications also fall within the scope of the present disclosure.

FIG. 7 is a flowchart illustrating an exemplary process 700 for dividing a time-varying motion signal according to some embodiments of the present disclosure. In some embodiments, at least part of the process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order of the operations of the process 700 as illustrated in FIG. 7 and described below is not intended to be limiting. In some embodiments, the operation 504 may be achieved according to the process 700.

In 702, the processing device 140 (e.g., the physiological motion dividing module 420) may obtain a time-varying motion signal representing the physiological motion via a sensor coupled to the subject.

The sensor may collect time-varying information relating to, for example, the respiration motion, the cardiac motion, etc., of the subject. The processing device 140 may further analyze the time-varying information to obtain the time varying motion signal including, for example, a respiration motion signal, a cardiac motion signal, etc.

In some embodiments, the sensor may be included in a motion monitoring system for monitoring the physiological motion of the subject. An exemplary motion monitoring system may include a respiration monitoring system, a cardiac monitoring system, or the like, or a combination thereof. Specifically, the sensor may include a motion detection device, such as a camera (e.g., an infrared camera), a belt secured around the chest of the subject, or another pressure measurement technique or device to measure the change of pressure during the breathing cycles of the subject.

In some embodiments, the sensor may detect the motion of the subject throughout the imaging procedure described in the present disclosure. The time-varying motion signal may be correlated with one or more images of the subject. In some embodiments, the one or more images may include cine images, or a 4D CT image of the subject. The correlation between the one or more images of the subject and the time-varying motion signal is achieved such that each single image frame in the one or more images is corresponding to a specific portion of the time-varying motion signal. In a further embodiment, the processing device 140 may establish a relationship between the time-varying motion signal and the axial positions of the ROI included in the one or more images.

In 704, the processing device 140 (e.g., the physiological motion dividing module 420) may divide the time-varying motion signal into a plurality of segments.

For illustration purpose, the time-varying motion signal represented by a time-varying motion waveform is taken as an example. The processing device 140 (e.g., the physiological motion dividing module 420) may divide the time-varying motion waveform into a plurality of segments. In some embodiments, the processing device 140 may divide the time-varying motion waveform according to an instruction from an operator (e.g., a technician, a doctor). For example, as instructed by the operator, the processing device 140 may evenly divide the time-varying motion waveform into segments such that the time bin corresponding to each segment has an identical time span. As another example, as instructed by the operator, the processing device 140 may unevenly divide the time-varying motion waveform into segments such that at least two segments may have different time spans. In some embodiments, the processing device 140 may divide the time-varying motion waveform into a plurality of segments using a segmenting model. Merely by way of example, the segmenting model may perform the segmentation according to the distribution of the waveform. For example, a segment at a sharply varying portion of the waveform may be assigned with a smaller time span, and a segment at a slowly varying portion of the waveform may be assigned with a larger time span. In some embodiments, one or more time-varying motion signal samples may be input to the segmenting model, with a plurality of labeled segments, to train a preliminary segmenting model. When a certain condition is satisfied (e.g., a preset iteration count of the training process is met), the trained preliminary segmenting model may be used as the segment model as described above.

It should be noted that the above descriptions of the process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, other techniques, rather than using a sensor, may be used to obtain the time-varying motion signal. For example, the time-varying motion signal may be derived from one or more images (e.g., cine images) of the subject by performing a scan on the subject in at least one full cycle of the physiological motion of the subject. The processing device 140 (e.g., the physiological motion dividing module 420) may extract the time-varying motion signal directly from the one or more images according to, for example, the motion states of the subject in the one or more images. In some embodiments, the process 700 may include one or more other operations. However, those variations and modifications also fall within the scope of the present disclosure.

Figure 8:
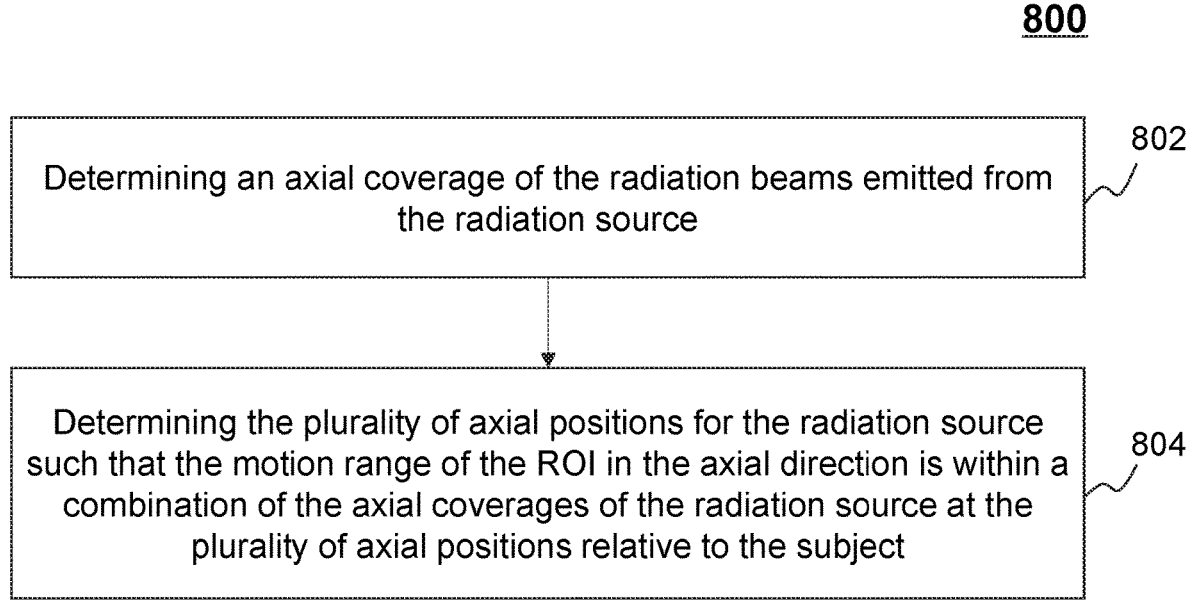
FIG. 8 is a flowchart illustrating an exemplary process for determining a plurality of axial positions for a radiation source according to some embodiments of the present disclosure.

FIG. 8 is a flowchart illustrating an exemplary process 800 for determining a plurality of axial positions for a radiation source according to some embodiments of the present disclosure. In some embodiments, at least part of the process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order of the operations of the process 800 as illustrated in FIG. 7 and described below is not intended to be limiting. In some embodiments, the operation 506 may be achieved according to the process 800.

In 802, the processing device 140 (e.g., e.g., the axial position determination module 430) may determine an axial coverage of the radiation beams emitted from the radiation source.

The axial coverage of the radiation beams may denote the spatial range of the radiation beams along an axis that is extending along the axial direction and traverses the isocenter of the imaging device 110. In some embodiments, the axial coverage of the radiation beams may also be referred to as the axial FOV of the radiation beams.

In 804, the processing device 140 (e.g., the axial position determination module 430) may determine the plurality of axial positions for the radiation source such that the motion range of the ROI in the axial direction is within a combination of the axial coverages of the radiation source at the plurality of axial positions relative to the subject.

In some embodiments, the processing device 140 (e.g., the axial position determination module 430) may determine the plurality of axial positions for the radiation source based on the motion range of the ROI in the axial direction and the axial coverage of the radiation beams emitted from the radiation source. For example, the processing device 140 (e.g., the axial position determination module 430) may determine a plurality of simulated axial positions, and determine a simulated combination of the axial coverages of the radiation beams emitted from the radiation source at the plurality of simulated axial positions relative to the subject. Then the processing device 140 (e.g., the axial position determination module 430) may compare the simulated combination of the axial coverages with the motion range of the ROI in the axial direction. Furthermore, the processing device 140 (e.g., the axial position determination module 430) may adjust the plurality of simulated axial positions based on the comparison result to determine the plurality of axial positions for the radiation source.

In some embodiments, the plurality of axial positions of the radiation source relative to the subject may vary in steps or continuously. For example, the plurality of axial positions relative to the subject may continuously change while the radiation source is emitting the radiation beams during each time bin. As another example, the plurality of axial positions relative to the subject may be discrete positions and the radiation source may emit the radiation beams only when it reaches the designated positions.

It should be noted that the above descriptions of the process 800 are provided for the purposes of illustration, and not intended to limit the scope of the present disclosure. For persons having ordinary skills in the art, various modifications and changes in the forms and details of the application of the above method and system may occur without departing from the principles of the present disclosure. For example, the motion range of the ROI in the axial direction may be replaced with the real-time axial range of the ROI in the axial direction. With the physiological motion, the real-time axial range of the ROI may change with time. The processing device 140 (e.g., the axial position determination module 430) may track the motion of the ROI in real time, and determine the plurality of axial positions relative to the subject based on the real-time axial range of the ROI. That is, the combination of the axial coverages of the radiation source at the plurality of axial positions relative to the subject may vary with time. In some embodiments, one or more operations described in the process 800 may be omitted.

FIG. 9 is a flowchart illustrating an exemplary process 900 for causing the radiation source to emit radiation beams according to some embodiments of the present disclosure In some embodiments, at least part of the process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 900 may be accomplished with one or more additional operations not described, and/or without one or more of the operations discussed. Additionally, the order of the operations of the process 900 as illustrated in FIG. 9 and described below is not intended to be limiting. In some embodiments, the operation 508 may be achieved according to the process 900.

In some embodiments, the subject may be supported by a table (e.g., the table 114 of the imaging device 110) that is movable in the axial direction. For example, in any one of a CT imaging, a PET-CT imaging system, and a CT-linac system, a table supporting the subject may be movable in the axial direction.

In 902, the processing device 140 (e.g., the radiation beam emitting module 440) may cause the table to move to a table location such that the radiation source is at one of the plurality of axial positions relative to the subject.

In some embodiments, the plurality of axial positions may be represented using one or more sets of coordinates. For example, the processing device 140 (e.g., the axial position determination module 430) may establish a coordinate system with the origin at, for example, the isocenter of the imaging device 110, the position of the radiation source (or a position on the gantry 113 of the imaging device 110). And the processing device 140 (e.g., the radiation beam emitting module 440) may cause the table to move to a table location based on the plurality of axial positions represented using the one or more sets of coordinates. In some embodiments, during each time bin as described in the present disclosure, the processing device 140 may cause the table to move to different table locations such that the radiation beams may completely cover the motion range (or the real-time axial range) of the ROI in the time bin.

In 904, the processing device 140 (e.g., the radiation beam emitting module 440) may cause the radiation source to emit the radiation beams to the ROI while the table is at the table location.

In some embodiments, the radiation source may generate X-rays with at least two different energy spectra. In a dual energy CT system with a single radiation source (e.g., the scanning source 115), an X-ray tube included in the single radiation source may generate X-rays with a power supply provided by a voltage generator. The power supply provided by the voltage generator may rapidly switch between a low and a high X-ray tube voltages, and then X-rays with two different energy spectra may be generated to perform a scan on the ROI. Alternatively or additionally, the single radiation source may have two or more focal spots on the anode such that the single radiation source may emit the radiation beams in different viewing angles. Alternatively, the single radiation source may be replaced with multiple radiation sources. Each of the multiple radiation source may emit X-rays in different viewing angles, with same or different energy spectra. Alternatively, a multilayer detector, where each detector layer exhibits a different energy response, may be used to achieve additional energy-spectrum-based contrast.

It should be noted that the above descriptions of the process 900 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 900 may include one or more other operations. However, those variations and modifications also fall within the scope of the present disclosure.

FIG. 10 is a flowchart illustrating an exemplary process 1000 for causing the radiation source to emit radiation beams according to some embodiments of the present disclosure In some embodiments, at least part of the process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1000 may be accomplished with one or more additional operations not described, and/or without one or more of the operations discussed. Additionally, the order of the operations of the process 1000 as illustrated in FIG. 10 and described below is not intended to be limiting. In some embodiments, the operation 508 may be achieved according to the process 1000.

In some embodiments, the radiation source may be installed on a gantry (e.g., the gantry 113 of the imaging device 110) that is movable in the axial direction. For example, in a CT-on-rails type system, a gantry may be movable in the axial direction.

In 1002, the processing device 140 (e.g., the radiation beam emitting module 440) may cause the gantry to move to a gantry location such that the radiation source is at one of the plurality of axial positions relative to the subject.

In some embodiments, the plurality of axial positions may be represented using one or more sets of coordinates. For example, the processing device 140 (e.g., the axial position determination module 430) may establish a coordinate system with the origin at, for example, the isocenter of the imaging device 110, a position on the table (e.g., a position on the table 114 of the imaging device 110). And the processing device 140 (e.g., the radiation beam emitting module 440) may cause the gantry to move to a gantry location based on the plurality of axial positions represented using the one or more sets of coordinates. In some embodiments, during each time bin as described in the present disclosure, the processing device 140 may cause the gantry to move to different gantry locations such that the radiation beams may completely cover the motion range (or the real-time axial range) of the ROI in the time bin.

In 1004, the processing device 140 (e.g., the radiation beam emitting module 440) may cause the radiation source to emit the radiation beams to the ROI while the gantry is at the gantry location. More descriptions regarding the emitting of the radiation beams may be found elsewhere in the present disclosure. See, e.g., FIG. 9 and the descriptions thereof.

It should be noted that the above descriptions of the process 1000 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 1000 may include one or more other operations. However, those variations and modifications also fall within the scope of the present disclosure.

Figure 11:
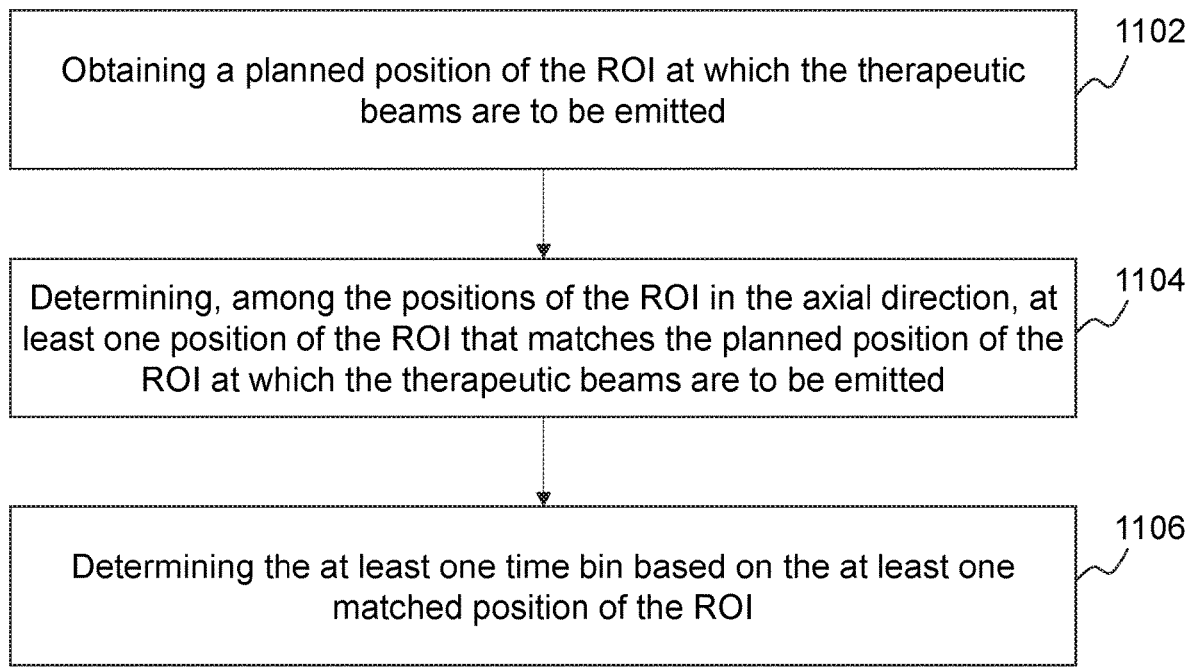
FIG. 11 is a flowchart illustrating an exemplary process for determining at least one time bin according to some embodiments of the present disclosure.

FIG. 11 is a flowchart illustrating an exemplary process 1100 for determining at least one time bin according to some embodiments of the present disclosure In some embodiments, at least part of the process 1100 may be performed by the processing device 140 (implemented in, for example, the computing device 200 shown in FIG. 2). For example, the process 1100 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 1100 may be accomplished with one or more additional operations not described, and/or without one or more of the operations discussed. Additionally, the order of the operations of the process 1100 as illustrated in FIG. 11 and described below is not intended to be limiting. In some embodiments, the operation 512 may be achieved according to the process 1100.

In 1102, the processing device 140 (e.g., the time bin determination module 460) may obtain a planned position of the ROI at which the therapeutic beams are to be emitted.

In some embodiments, the planned position of the ROI at which the therapeutic beams are to be emitted may be set in a predetermined treatment plan. For example, an operator may determine the planned position of the ROI at which the therapeutic beams are to be emitted based on a previous CT scan. In some embodiments, the planned position of the ROI may include a position of the ROI relative to other organs/tissues in the subject, a position of the ROI relative to the radiation source that emits the therapeutic beams, a position of the ROI relative to other components of the imaging device 110 (e.g., the gantry 113), or the like, or a combination thereof. Information (e.g., one or more set of coordinates) related to the planned position may be stored in a storage device (e.g., the storage device 150, the storage 220, the storage 390). The processing device 140 (e.g., the time bin determination module 460) may obtain the planned position of the ROI at which the therapeutic beams are to be emitted from storage device.

In 1104, the processing device 140 (e.g., the time bin determination module 460) may determine, among the positions of the ROI in the axial direction, at least one position of the ROI that matches the planned position of the ROI at which the therapeutic beams are to be emitted.

In some embodiments, the positions of the ROI in the axial direction may be determined as described elsewhere in the disclosure (e.g., the operation 510). For example, the processing device 140 may determine the positions of the ROI in the axial direction by identifying the ROI in the image frames generated according to the "exhaustive scan" or the "predictive scan" in each time bin.

In some embodiments, the position of the ROI in the axial direction matches the planned position of the ROI may denote that the axial position of the ROI relative to another organ/tissue in the subject may be same as the planned axial position of the ROI relative to the same organ/tissue in the subject. In some embodiments, the processing device 140 (e.g., the time bin determination module 460) may obtain an image of the ROI at the planned position (e.g., the plan image), and compare it with image frames corresponding to different time bins and different positions of the ROI in the axial direction. If the image of the ROI at the planned position coincides with a specific image frame (e.g., the positions of the ROI in two images coincides with each other), the processing device 140 (e.g., the time bin determination module 460) may determine the position of the ROI in the specific image frame as one of the at least one position of the ROI that matches the planned position of the ROI at which the therapeutic beams are to be emitted.

In 1106, the processing device 140 (e.g., the time bin determination module 460) may determine the at least one time bin based on the at least one matched position of the ROI.

As described elsewhere in the present disclosure, for each of the plurality time bins in a full cycle of the physiological motion, a position of the ROI in the axial direction may be determined. Additionally, the relationship between the positions of the ROI in the axial direction and the physiological motion (e.g., represented by a time-varying motion signal) may be established. The processing device 140 may determine the at least one time bin corresponding to the at least one matched position of the ROI based on the relationship.

In some embodiments, after the at least one time bin is determined, the processing device 140 may cause the imaging device 110 (e.g., the table 114) to move the subject to the treatment position, and the therapeutic beams may be emitted for the planned position of the ROI within time intervals corresponding to the at least one time bin. As used herein, if a time interval and the at least one time bin correspond to a same phase of the physiological motion (e.g., the respiration motion, the cardiac motion), the time interval may be deemed as corresponding to the at least one time bin.

It should be noted that the above descriptions of the process 1100 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the process 1100 may include one or more other operations. However, those variations and modifications also fall within the scope of the present disclosure. For example, the operations illustrated in the process 1100 may be applied in other applications including, for example, surgical interventions, and treatments such as a high intensity focused ultrasound (HIFU), a hyperthermia therapy, a brachytherapy, a cryotherapy, or the like, or any combination thereof.

In the scope of application of the above descriptions to therapy with beams originating external to the patient, it will be recognized that therapeutic beams may enter the patient from one or more angles, or over one or more continuous angular ranges. It will furthermore be recognized that by imaging a ROI, which has a component of motion in the axial direction, from the angles at which the external therapy beams will enter the patient, that the motion trajectory of the ROI may be most relevantly determined from the point-of-view corresponding to the beam angle(s)/beam angular range(s) of the planned therapeutic beam entry (beam's-eye-view imaging). Such therapeutic beams may include x-ray beams, charged particle beams, neutron beams, ultrasound beams, etc.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having at least one storage device storing a set of instructions, and at least one processor in communication with the at least one storage device, the method comprising:
   determining a motion range of a region of interest (ROI) of a subject in an axial direction, wherein the ROI moves due to a physiological motion of the subject;
   dividing the physiological motion into a plurality of time bins;
   in at least one of the plurality of time bins,
      determining, for a radiation source, a plurality of axial positions relative to the subject; and
      causing the radiation source to emit, at each of the plurality of axial positions relative to the subject, radiation beams to the ROI to generate an image frame of the ROI, wherein the radiation beams corresponding to the plurality of axial positions jointly cover the motion range of the ROI in the axial direction; and
   determining, for each of the plurality of time bins, a position of the ROI in the axial direction based on the image frames of the ROI generated in the corresponding time bin; and determining, based on the positions of the ROI in the axial directions and among the plurality of time bins, at least one time bin in which therapeutic beams are to be emitted to the ROI.

2. The method of claim 1, wherein the determining a motion range of an ROI of a subject in an axial direction comprises:
obtaining an image of the subject based on a scan of the subject;
identifying the ROI in the image of the subject; and
determining the motion range of the ROI based on the identified ROI.

3. The method of claim 1, wherein the physiological motion of the subject includes at least one of a respiration motion or a cardiac motion of the subject.

4. The method of claim 1, wherein the radiation source generates X-rays with at least two different energy spectra.

5. The method of claim 1, wherein the dividing the physiological motion into a plurality of time bins comprises:
obtaining a time-varying motion signal representing the physiological motion via a sensor coupled to the subject; and
dividing the time-varying motion signal into a plurality of segments, each of the plurality of the segments corresponding to one of the plurality of time bins.

6. The method of claim 1, wherein the determining, for a radiation source, a plurality of axial positions relative to the subject comprises:
determining an axial coverage of the radiation beams of the radiation source; and
determining the plurality of axial positions for the radiation source such that the motion range of the ROI in the axial direction is within a combination of the axial coverages of the radiation source at the plurality of axial positions relative to the subject.

7. The method of claim 1, wherein the subject is supported by a table that is movable in the axial direction, wherein the causing the radiation source to emit, at each of the plurality of axial positions relative to the subject, radiation beams to the ROI to generate an image frame of the ROI comprises:
causing the table to move to a table location such that the radiation source is at one of the plurality of axial positions relative to the subject; and
causing the radiation source to emit the radiation beams to the ROI while the table is at the table location.

8. The method of claim 1, wherein the radiation source is installed on a gantry that is movable in the axial direction, wherein the causing the radiation source to emit, at each of the plurality of axial positions relative to the subject, radiation beams to the ROI to generate an image frame of the ROI comprises:
causing the gantry to move to a gantry location such that the radiation source is at one of the plurality of axial positions relative to the subject; and
causing the radiation source to emit the radiation beams to the ROI while the gantry is at the gantry location.

9. The method of claim 1, wherein the determining, based on the positions of the ROI in the axial directions and among the plurality of time bins, at least one time bin, in which therapeutic beams are to be emitted to the ROI comprises:
obtaining a planned position of the ROI at which the therapeutic beams are to be emitted;
determining, among the positions of the ROI in the axial direction, at least one position of the ROI that matches the planned position of the ROI at which the therapeutic beams are to be emitted; and
determining the at least one time bin based on the at least one matched position of the ROI.

10. The method of claim 1, further comprising:
tracking a motion of the ROI, wherein the determining, for a radiation source, a plurality of axial positions relative to the subject comprises:
determining the plurality of axial positions relative to the subject based on the tracked motion of the ROI.

11. The method of claim 1, wherein the causing the radiation source to emit, at each of the plurality of axial positions relative to the subject, radiation beams to the ROI to generate an image frame of the ROI comprises:
causing the radiation source to emit, at each of the plurality of axial positions relative to the subject, radiation beams to the ROI from one or more angles at which the therapeutic beams are to be emitted to the ROI.

12. A system, comprising:
at least one storage medium including a set of instructions; and
at least one processor in communication with the at least one storage medium, wherein when executing the instructions, the at least one processor is configured to direct the system to perform operations including:
determining a motion range of a region of interest (ROI) of a subject in an axial direction, wherein the ROI moves due to a physiological motion of the subject;
dividing the physiological motion into a plurality of time bins;
in at least one of the plurality of time bins,
determining, for a radiation source, a plurality of axial positions relative to the subject; and
causing the radiation source to emit, at each of the plurality of axial positions relative to the subject, radiation beams to the ROI to generate an image frame of the ROI, wherein the radiation beams corresponding to the plurality of axial positions jointly cover the motion range of the ROI in the axial direction; and
determining, for each of the plurality of time bins, a position of the ROI in the axial direction based on the image frames of the ROI generated in the corresponding time bin; and
determining, based on the positions of the ROI in the axial directions and among the plurality of time bins, at least one time bin in which therapeutic beams are to be emitted to the ROI.

13. The system of claim 12, wherein the determining a motion range of an ROI of a subject in an axial direction comprises:
obtaining an image of the subject based on a scan of the subject;
identifying the ROI in the image of the subject; and
determining the motion range of the ROI based on the identified ROI.

14. The system of claim 12, wherein the physiological motion of the subject includes at least one of a respiration motion or a cardiac motion of the subject.

15. The system of claim 12, wherein the radiation source generates X-rays with at least two different energy spectra.

16. The system of claim 12, wherein the dividing the physiological motion into a plurality of time bins comprises:
obtaining a time-varying motion signal representing the physiological motion via a sensor coupled to the subject; and dividing the time-varying motion signal into a plurality of segments, each of the plurality of segments corresponding to one of the plurality of time bins.

17. The system of claim 12, wherein the determining, for a radiation source, a plurality of axial positions relative to the subject comprises:
   determining an axial coverage of the radiation beams of the radiation source; and
   determining the plurality of axial positions for the radiation source such that the motion range of the ROI in the axial direction is within a combination of the axial coverages of the radiation source at the plurality of axial positions relative to the subject.

18. The system of claim 12, wherein the determining, based on the positions of the ROI in the axial directions and among the plurality of time bins, at least one time bin, in which therapeutic beams are to be emitted to the ROI comprises:
   obtaining a planned position of the ROI at which the therapeutic beams are to be emitted;
   determining, among the positions of the ROI in the axial direction, at least one position of the ROI that matches the planned position of the ROI at which the therapeutic beams are to be emitted; and
   determining the at least one time bin based on the at least one matched position of the ROI.

19. The system of claim 12, further comprising:
   tracking a motion of the ROI, wherein the determining, for a radiation source, a plurality of axial positions relative to the subject comprises:
      determining the plurality of axial positions relative to the subject based on the tracked motion of the ROI.

20. The system of claim 12, wherein the causing the radiation source to emit, at each of the plurality of axial positions relative to the subject, radiation beams to the ROI to generate an image frame of the ROI comprises:
   causing the radiation source to emit, at each of the plurality of axial positions relative to the subject, radiation beams to the ROI from one or more angles at which the therapeutic beams are to be emitted to the ROI.

* * * * *